United States Patent
Wu et al.

(10) Patent No.: US 8,886,323 B2
(45) Date of Patent: Nov. 11, 2014

(54) ELECTRICAL BRAIN STIMULATION IN GAMMA BAND

(75) Inventors: Jianping Wu, Shoreview, MN (US); Dwight E. Nelson, Shoreview, MN (US); Rahul Gupta, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 568 days.

(21) Appl. No.: 12/701,099

(22) Filed: Feb. 5, 2010

(65) Prior Publication Data
US 2011/0196446 A1 Aug. 11, 2011

(51) Int. Cl.
*A61N 1/05* (2006.01)
*A61N 1/36* (2006.01)
*A61B 5/048* (2006.01)

(52) U.S. Cl.
CPC ............. *A61N 1/36067* (2013.01); *A61B 5/048* (2013.01); *A61N 1/0534* (2013.01); *A61N 1/36171* (2013.01)
USPC .......................................................... 607/45

(58) Field of Classification Search
USPC .......................................................... 607/45
See application file for complete search history.

(56) References Cited

U.S. PATENT DOCUMENTS

| | | | |
|---|---|---|---|
| 6,463,328 B1 | 10/2002 | John | |
| 7,305,268 B2 | 12/2007 | Gliner et al. | |
| 7,346,382 B2 | 3/2008 | McIntyre et al. | |
| 7,483,747 B2 | 1/2009 | Gliner et al. | |
| 2006/0015153 A1* | 1/2006 | Gliner et al. | 607/45 |
| 2006/0258950 A1 | 11/2006 | Hargrove et al. | |
| 2006/0276853 A1 | 12/2006 | Tass et al. | |
| 2007/0032834 A1 | 2/2007 | Gliner et al. | |
| 2007/0142874 A1 | 6/2007 | John | |
| 2007/0167991 A1 | 7/2007 | DiLorenzo | |
| 2007/0225674 A1 | 9/2007 | Molnar et al. | |
| 2008/0033502 A1 | 2/2008 | Harris et al. | |
| 2008/0319511 A1 | 12/2008 | Pless | |
| 2009/0082691 A1 | 3/2009 | Denison et al. | |
| 2009/0118787 A1* | 5/2009 | Moffitt et al. | 607/45 |

FOREIGN PATENT DOCUMENTS

WO    WO 2007/089394 A2    8/2007

OTHER PUBLICATIONS

Mwiza Ushe et al., "Effect of Stimulation Frequency on Tremor Suppression in Essential Tremor," Movement Disorders, vol. 19, No. 10, 2004, pp. 1163-1168.
Alexis M. Kuncel et al., "Amplitude- and Frequency-Dependent Changes in Neuronal Regularity Parallel Changes in Tremor With Thalamic Deep Brain Stimulation," IEEE Transactions on Neural Systems and Rehabilitation Engineering, vol. 15, No. 2, Jun. 2007, pp. 190-197.
Alexis M. Kuncel et al., "Myoclonus and tremor response to thalamic deep brain stimulation parameters in a patient with inherited myoclonus-dystonia syndrome," Clinical Neurology and Neurosurgery 111, 2009, pp. 303-306.
Notification of Transmittal of the International Search Report and Written Opinion for patent application No. PCT/US2011/023307, mailed Apr. 21, 2011, 13 pages.

* cited by examiner

*Primary Examiner* — Paula J Stice
(74) *Attorney, Agent, or Firm* — Shumaker & Sieffert, P.A.

(57) ABSTRACT

This disclosure describes techniques for delivering electrical stimulation to the brain of a patient at a frequency greater than a selected frequency. The techniques may reestablish gamma frequency band activity within the brain of a patient, and thus improve the patient's movements and cognitive states. In one example, the disclosure is directed to a method that includes selecting a frequency within a gamma frequency band and delivering electrical stimulation at a frequency greater than the selected frequency.

47 Claims, 6 Drawing Sheets

ELECTRICAL BRAIN STIMULATION IN GAMMA BAND

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) by a medical device to one or more sites in a patient, such as a brain, spinal cord, leg muscle or arm muscle, in a patient may help alleviate, and in some cases, eliminate symptoms associated with movement disorders.

SUMMARY

In general, the disclosure is directed toward techniques for delivering electrical stimulation to the brain of a patient at one or more frequencies at a specified level greater than a selected frequency in the gamma band. The stimulation may include, for example, pulses or continuous waveforms with one or more frequencies greater than the selected frequency in the gamma band. In some examples, if desired gamma frequency activity has been modified, disrupted or compromised, the techniques may reestablish desired gamma frequency band activity within the brain of a patient, and thereby improve or maintain the patient's movements and/or cognitive states.

In one example, the disclosure is directed to a method comprising selecting a frequency within a gamma frequency band and delivering electrical stimulation at a frequency greater than the selected frequency.

In another example, the disclosure is directed to a device comprising an implantable housing, one or more leads coupled to the housing, one or more electrodes carried by the one or more leads, and a processor configured to select a frequency within a gamma frequency band and control delivery of electrical stimulation at a frequency greater than the selected frequency.

In another example, the disclosure is directed to a computer-readable storage medium comprising instructions that, when executed by a processor, cause the processor to select a frequency within a gamma frequency band and control delivery of electrical stimulation at a frequency greater than the selected frequency.

In another example, the disclosure is directed to a device comprising means for selecting a frequency within a gamma frequency band and means for delivering electrical stimulation at a frequency greater than the selected frequency.

The details of one or more aspects of the disclosure are set forth in the accompanying drawings and the description below. Other features, objects, and advantages will be apparent from the description and drawings, and from the claims.

DETAILED DESCRIPTION

Figure 1:
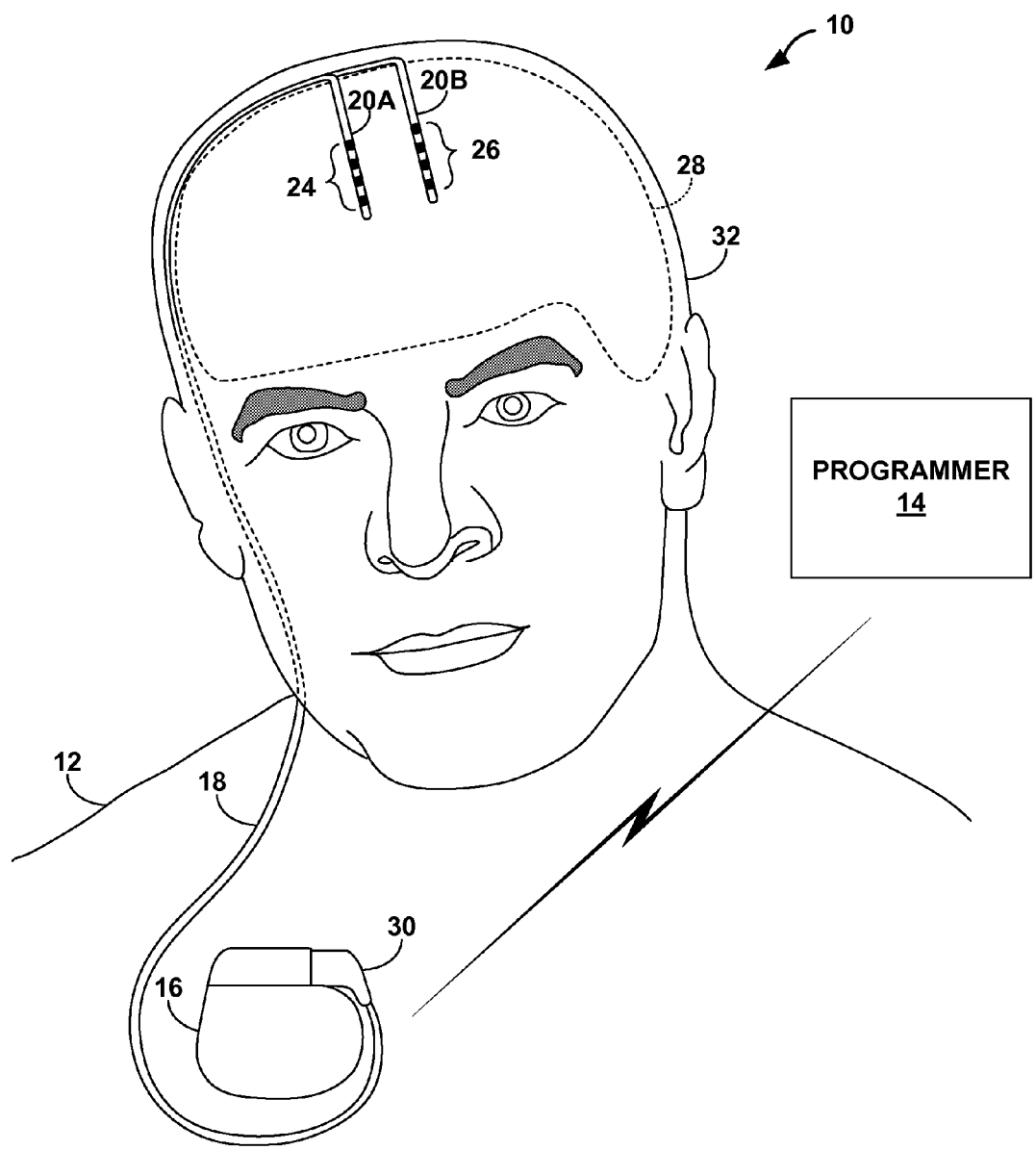
FIG. 1 is a conceptual diagram illustrating an example deep brain stimulation (DBS) system that may be used to implement the techniques of this disclosure.

This disclosure describes techniques for improving entrainment and synchronization of brain activity. Brain activity may be recorded, for example, in the form of local field potential (LFP) and/or electroencephalogram (EEG) or electrocorticogram (ECoG) sensed by an implantable or external medical device. Entrainment generally refers to the process of using stimuli to affect brain activity, e.g., oscillations within a frequency band in the brain. Gamma frequency band oscillations, e.g., ordinarily between about 35 Hertz (Hz) and about 120 Hz or more, in the central nervous system (CNS), recorded using LFP and EEG, for example, are associated with normal information processing in movement and sensory structures. Beta frequency band oscillations between about 8 Hz and about 35 Hz, have been associated with dysfunctions of CNS circuits that control behavioral movements and cognitive states. Higher frequency stimulation, e.g., about 130 Hz, of subcortical brain areas involved with movement, e.g., subthalamic nucleus, globus pallidus internus, and ventralis intermedius nucleus of the thalamus, may reduce behaviors associated with essential tremor and Parkinson's disease such as rigidity, bradykinesia and tremor.

Using the techniques of this disclosure, entrainment or synchronization of brain LFP or EEG activity may be improved by delivering electrical stimulation to the brain of a patient at one or more frequencies at a specified level greater than a selected frequency in the gamma band. For the purposes of this disclosure entrainment of brain LFP is regarded as a temporal matching between a periodic stimulation and an endogenous brain oscillation or similar matching between multiple brain areas. Synchronization is regarded as spontaneous or induced temporal alignment of brain oscillations. The stimulation may include, for example, pulses or continuous waveforms with one or more frequencies greater than the selected frequency in the gamma band. In some examples, the gamma band frequency may be selected based on an assumption of a typical gamma band frequency for a human patient, i.e., a representative gamma band frequency, or based on a patient-specific gamma band frequency determined for a particular patient to which the stimulation is to be delivered. The gamma band frequency may be, for example, a gamma band center frequency, representing a frequency at which gamma band activity is centered.

In one example, stimulation may be delivered by electrically sweeping a frequency, e.g., a pulse frequency, of delivered electrical stimulation across a range of frequencies, and monitoring a response of the patient. As an example, sweeping the frequency of the stimulation may be achieved by decreasing the stimulation frequency from a frequency that is some margin that is greater than the patient's specific gamma frequency or representative gamma frequency to a frequency that is near the patient's specific or representative gamma frequency. In another example, sweeping the frequency of the stimulation may be achieved by increasing the stimulation frequency from a frequency that is near the patient's specific or representative gamma frequency to a frequency that is some margin that is greater than a patient's specific gamma frequency or representative gamma frequency. In another example, stimulation may be delivered at a frequency that is some margin that is greater than the patient's specific gamma frequency or representative gamma frequency, e.g., 1.05 times to 3 times the patient's specific gamma frequency. In either case, the stimulation may be delivered for a selected duration, and may have various stimulation parameters selected to support entrainment and synchronization.

During or after the delivery of the electrical stimulation, monitoring patient behavior, e.g., movements in a medical device implantation session or a follow-up office visit, or CNS effects, e.g., reduction of beta frequency band activity or recovery of the patient's specific gamma frequency band activity, may allow the electrical stimulation delivery device to cycle delivery of electrical stimulation in order to achieve lower power consumption and improved therapeutic benefit. Entrainment durations and duty cycles may be timed or titrated to increase battery life, maintain gamma frequency band rhythm, reduce beta frequency band rhythm, and/or improve therapeutic benefit.

The delivered electrical stimulation may be in the form of pulses or a continuous waveform. As such, the frequency of the delivered electrical stimulation may refer to the frequency of a pulse or the frequency of a continuous waveform. Stimulation parameters such as voltage or current amplitude, electrode combinations and polarity, and, if applicable, pulse width, may all be adjusted in order to provide efficacious treatment to the patient.

FIG. 1 is a conceptual diagram illustrating an example deep brain stimulation (DBS) system that may be used to implement the techniques of this disclosure. In FIG. 1, example therapy system 10 may deliver electrical stimulation therapy to control a patient condition, such as a movement disorder or a neurodegenerative impairment of patient 12. Patient 12 ordinarily will be a human patient. In some cases, however, therapy system 10 may be applied to other mammalian or non-mammalian non-human patients. While movement disorders and neurodegenerative impairment are primarily referred to in this disclosure, in other examples, therapy system 10 may provide therapy to manage symptoms of other patient conditions, such as, but not limited to, seizure disorders or psychological disorders.

A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions. Although movement disorders are primarily referred to throughout the remainder of the disclosure, the therapy systems and methods described herein are also useful for controlling symptoms of other conditions, such as neurodegenerative impairment.

In the example of FIG. 1, therapy system 10 includes medical device programmer 14, implantable medical device (IMD) 16, lead extension 18, and leads 20A and 20B with respective sets of electrodes 24, 26. In the example shown in FIG. 1, electrodes 24, 26 of leads 20A, 20B are positioned to deliver electrical stimulation to a tissue site within brain 28, such as a deep brain site under the dura mater of brain 28 of patient 12. In some examples, delivery of stimulation to one or more regions of brain 28, such as the subthalamic nucleus, globus pallidus internus or thalamus, may be an effective treatment to manage movement disorders, such as Parkinson's disease or essential tremor.

IMD 16 includes a therapy module that includes a stimulation generator that generates and delivers electrical stimulation therapy to patient 12 via a subset of electrodes 24, 26 of leads 20A and 20B, respectively. The subset of electrodes 24, 26 that are used to deliver electrical stimulation to patient 12, and, in some cases, the polarity of the subset of electrodes 24, 26, may be referred to as a stimulation electrode combination.

Using the techniques described in this disclosure, a subset of electrodes 24, 26 of leads 20A and 20B, respectively, may be used to deliver electrical stimulation to patient 12 in order to re-establish, or re-induce, gamma frequency band activity within brain 28. As mentioned above, gamma frequency band activity may be facilitative of movement and cognitive states, while beta frequency band activity may be inhibitive of movement and perhaps cognitive states. As such, it may be desirable to decrease beta frequency band activity in the brain and increase gamma frequency band activity in the brain.

In some examples, beta frequency band activity in the brain may be decreased and gamma frequency band activity in the brain may be increased by delivering electrical stimulation to a portion of the brain at a frequency some margin that is greater than a gamma band frequency. In one example, the frequency of the electrical stimulation delivered to the portion of the brain may be a constant frequency at some margin that is greater than a gamma band frequency. For example, electrodes 24, 26 of leads 20A and 20B, respectively, may be used to deliver electrical stimulation to patient 12 at a frequency that is between about 1.05 times and 3 times a patient-specific or representative gamma band frequency. Again, the gamma frequency band may include gamma band frequencies between about 35 Hz and about 120 Hz. As one example, electrodes 24, 26 of leads 20A and 20B may deliver electrical stimulation to patient 12 at a frequency that is 1.1 times a gamma band frequency of 70 Hz, for example. Thus, electrodes 24, 26 of leads 20A and 20B may deliver electrical stimulation to patient 12 at a frequency of about 77 Hz, which may be effective in re-inducing desired gamma frequency band activity, and perhaps also reducing or eliminating pathological Beta band activities. Re-inducing gamma band activity refers to increasing the power in the gamma frequency band. In some instances, re-inducing gamma band activity may be accompanied by a decrease in the activity at other frequencies.

In another example, the frequency of the electrical stimulation delivered to the portion of the brain may be applied in a sweeping manner. For example, the frequency of the electrical stimulation may be swept through a range of frequency values. In a frequency sweep, the frequency of the electrical stimulation may begin at one value and then may be varied, e.g., increased or decreased, from a first frequency to a second frequency. For example, electrodes 24, 26 of leads 20A and 20B, respectively, may be used to deliver electrical stimulation to patient 12 that begins at a frequency that is between about 1.05 times and 3 times a gamma band frequency and extends upward to another, higher frequency that is between 1.05 times and 3 times a gamma band frequency, or downward to another, lower frequency that is between 1.05 times and 3 times a gamma band frequency. In some cases, in downward sweeping, the frequency may be swept downward from a frequency that is between 1.05 times and 3 times a gamma band frequency to a lower frequency that is at or near the gamma band frequency. As one example, electrodes 24, 26 of leads 20A and 20B may begin delivering electrical stimulation to patient 12 at a frequency that is 2 times a gamma band frequency of 70 Hz, for example, and then sweep the frequency of the delivered electrical stimulation downward from 140 Hz toward the gamma band frequency of 70 Hz while delivering electrical stimulation. It should be noted that in some examples, the frequency may be swept back and forth between a first frequency and a second frequency.

In some examples, the electrical stimulation may be swept upwards. For example, electrical stimulation may be delivered in a sweeping manner from a low gamma band frequency to a gamma band frequency (e.g., from about 35 Hz to about 135 Hz or less) while simultaneously monitoring LFP or EEG activity.

It should be noted that leads 20A, 20B may be separate leads, or bifurcated segments on a single lead. Some example configurations may comprise only a single lead. Two leads support bilateral stimulation in both brain hemispheres while one lead supports unilateral stimulation in one hemisphere. In a frequency sweep, stimulation may be applied at different frequencies in a range of frequencies in a sequence, e.g., by increasing or decreasing by N Hz, in a linear or non-linear manner.

Figure 2:
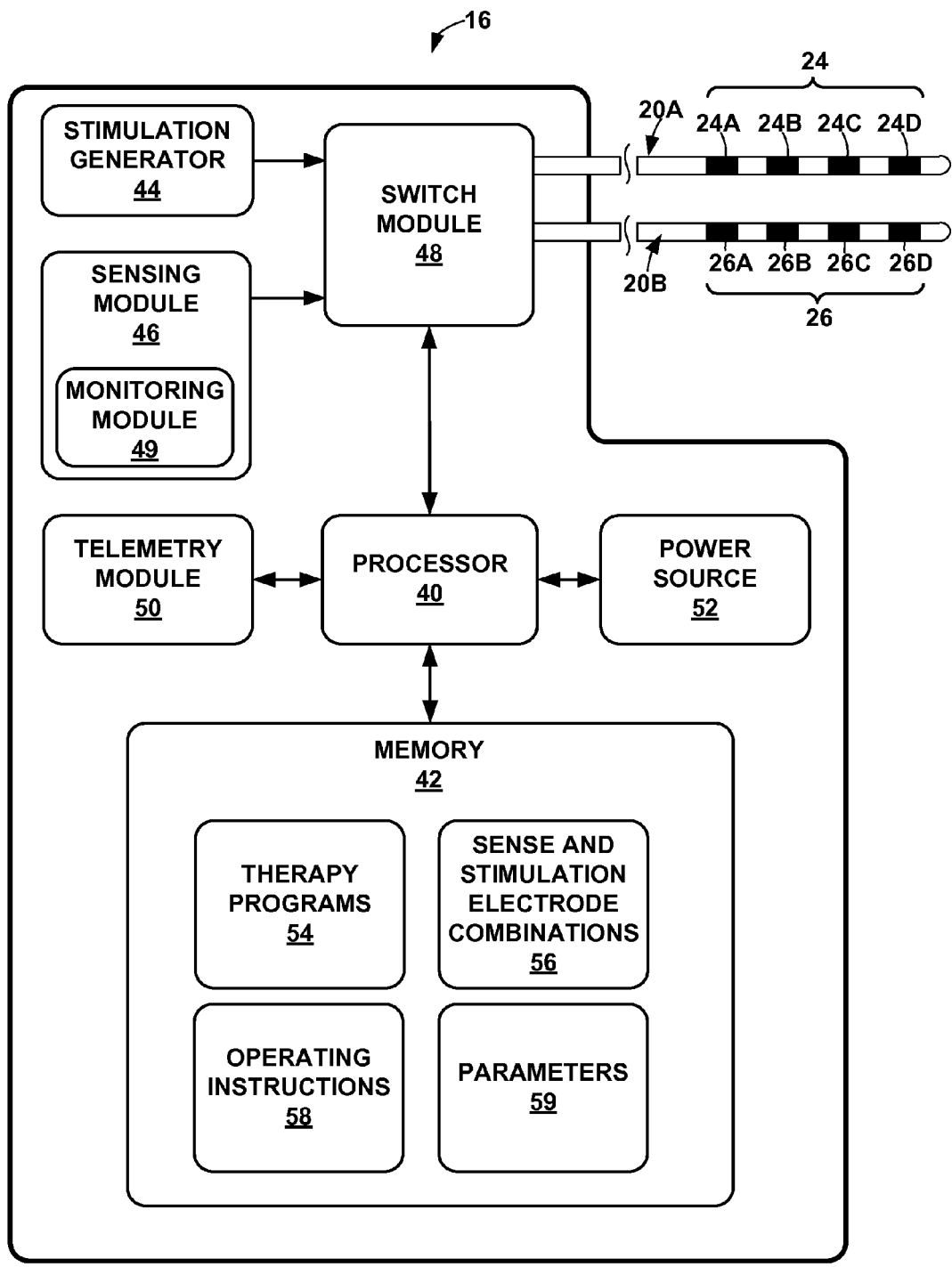
FIG. 2 is functional block diagram illustrating components of an example medical device that may be used to implement the techniques of this disclosure.

FIG. 2 is functional block diagram illustrating components of an example medical device that may be used to implement the techniques of this disclosure. FIG. 2 is a functional block diagram illustrating components of an example IMD 16. In the example shown in FIG. 2, IMD 16 includes processor 40, memory 42, stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions.

In the example shown in FIG. 2, memory 42 stores therapy programs 54, sense electrode combinations and associated stimulation electrode combinations 56, and operating instructions 58 in separate memories within memory 42. Each stored therapy program 54 defines a particular program of therapy in terms of respective values for electrical stimulation parameters, such as a stimulation electrode combination, electrode polarity, current or voltage amplitude, pulse width, and pulse rate. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis. It should be noted that an algorithm to select a frequency within the gamma frequency band may be and track the frequency may be stored in memory 42, or another memory within IMD 16 or programmer 14.

Sense and stimulation electrode combinations 56 stores sense electrode combinations and associated stimulation electrode combinations. As described above, in some examples, the sense and stimulation electrode combinations may include the same subset of electrodes 24, 26, or may include different subsets of electrodes. Operating instructions 58 guide general operation of IMD 16 under control of processor 40, and may include instructions for measuring the impedance of electrodes 24, 26. Processor 40 may compare received bioelectrical brain signals to values stored as parameters 59, as will be discussed in more detail below.

Stimulation generator 44, under the control of processor 40, generates stimulation signals for delivery to patient 12 via selected combinations of electrodes 24, 26. An example range of electrical stimulation parameters believed to be effective in DBS to manage a movement disorder of patient include the following:

1. Frequency: between approximately 20 Hz and approximately 500 Hz, such as approximately 130 Hz.
2. Voltage Amplitude: between approximately 0.1 volts and approximately 20 volts, such as between approximately 0.5 volts and approximately 10 volts, or approximately 5 volts.
3. Current Amplitude: A current amplitude may be defined as the biological load in which the voltage is delivered. In a current-controlled system, the current amplitude, assuming a lower level impedance of approximately 500 ohms, may be between approximately 0.2 milliamps to approximately 100 milliamps, such as between approximately 1 milliamps and approximately 40 milliamps, or approximately 10 milliamps. However, in some examples, the impedance may range between about 200 ohms and about 2 kilohms.
4. Pulse Width: between approximately 10 microseconds and approximately 5000 microseconds, such as between approximately 100 microseconds and approximately 1000 microseconds, or between approximately 180 microseconds and approximately 450 microseconds.

Stimulation generator 60 may, for example, generate either constant current-based or constant voltage-based stimulation in the form of pulses or continuous waveforms. In delivering constant current-based stimulation, stimulation generator 60 maintains the amplitude of the current at a constant level. In delivering constant voltage-based stimulation, stimulation generator 60 maintains the amplitude of the voltage at a constant level.

Accordingly, in some examples, stimulation generator 44 generates electrical stimulation signals in accordance with the electrical stimulation parameters noted above. Other ranges of therapy parameter values may also be useful, and may depend on the target stimulation site within patient 12, which may be within brain 28 or other portions of the nervous system. While stimulation pulses are described, stimulation signals may be of any form, such as continuous-time signals (e.g., sine waves) or the like.

Processor 40 may include any one or more of a microprocessor, a controller, a digital signal processor (DSP), an application specific integrated circuit (ASIC), a field-programmable gate array (FPGA), discrete logic circuitry, and the functions attributed to processor 40 in this disclosure may be embodied as firmware, hardware, software or any combination thereof. Processor 40 controls stimulation generator 44 according to therapy programs 52 stored in memory 42 to deliver, or apply, particular stimulation parameter values specified by one or more of programs, such as amplitude, pulse width, and pulse rate.

In the example shown in FIG. 2, the set of electrodes 24 includes electrodes 24A, 24B, 24C, and 24D, and the set of electrodes 26 includes electrodes 26A, 26B, 26C, and 26D. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48.

Stimulation generator 44 may be a single channel or multi-channel stimulation generator. In particular, stimulation generator 44 may be capable of delivering a single stimulation pulse, multiple stimulation pulses or continuous signal at a given time via a single electrode combination, or multiple stimulation pulses or continuous signals at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Sensing module 46, under the control of processor 40, may sense bioelectrical brain signals and provide the sensed bioelectrical brain signals to processor 40. Processor 40 may control switch module 48 to couple sensing module 46 to selected combinations of electrodes 24, 26, i.e., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signals sensed across the selected electrodes 24, 26 to sensing module 46. The bioelectrical brain signals may include biomarkers, e.g., amplitude and phase relationships, which are indicative of electrical activity within brain 28 of patient 12 and, in particular, electrical activity within one or more frequency bands, e.g., gamma frequency band, beta frequency band, theta frequency band (about 4 Hz to about 7 Hz), and other frequency bands, of brain 28.

Although sensing module 46 is incorporated into a common housing with stimulation generator 44 and processor 40 in FIG. 2, in other examples, sensing module 46 may be in a separate housing from IMD 16 and may communicate with processor 40 via wired or wireless communication techniques. Example bioelectrical brain signals include, but are not limited to, a signal generated from local field potentials within one or more regions of brain 28. EEG and ECoG signals are examples of local field potentials (LFPs) that may be measured from brain 28. However, local field potentials may include a broader genus of electrical signals within brain 28 of patient 12.

In accordance with the techniques of this disclosure, processor 40 may select a frequency within a frequency band of patient 12 and control delivery of electrical stimulation at a frequency greater than the selected frequency. In one example, processor 40 may select a patient-specific frequency within a frequency band, e.g., the gamma frequency band, by analyzing bioelectrical brain signals sensed across the selected electrodes 24, 26. For instance, processor 40 may analyze bioelectrical brain signals sensed across the selected electrodes 24, 26 and select that a specific patient 12 has oscillations of 70 Hz within the gamma frequency band.

In another example, processor 40 may select a representative frequency within a frequency band, e.g., the gamma frequency band, rather than a patient-specific frequency. That is, given certain characteristics of a patient, such as age and sex, disease severity, type of symptoms, medication state, behavioral, psychological, and/or physical state, the frequency within the frequency band may be selected based on the basic body model. Thus, in some examples, the frequency may be selected using a model, while in other examples, the frequency may be selected via sensed bioelectrical brain signals of patient 12.

After selecting the frequency within the frequency band, processor 40 may control stimulation generator 44 to deliver electrical stimulation at a frequency greater than the selected frequency, e.g., above 70 Hz. In one example, processor 40 may control stimulation generator 44 to deliver electrical stimulation to patient 12 via electrodes 24, 26 at a frequency that is between a range of about 1.05 times and about 3 times the selected frequency, e.g., about 1.05 times to about 3 times the selected frequency of 70 Hz. Thus, in order to re-induce or increase power of gamma frequency band activity within patient 12, processor 40 may, in one specific example, control delivery of electrical stimulation to patient 12 at a frequency that is 1.1 times a selected frequency of about 70 Hz, or about 77 Hz. Re-inducing gamma frequency band activity within patient 12 may facilitate movement and cognitive states.

In some examples, processor 40 may control stimulation generator 44 to begin delivering via electrodes 24, 26 electrical stimulation to patient 12 at a second frequency that is between a range of about 1.05 times and about 3 times the selected first frequency, e.g., 1.05 times to 3 times the selected first frequency of 70 Hz, and then sweep the frequency of delivered electrical stimulation downward from the second frequency to a frequency near the selected first frequency (or sweep the second frequency upward toward a third frequency within a range between about 1.05 to about 3 times the selected frequency). By way of specific example, processor 40 may control stimulation generator 44 to begin delivering via electrodes 24, 26 electrical stimulation to patient 12 at a second frequency of about 77 Hz (1.1 times an example selected first frequency of 70 Hz) and then sweep the frequency of the applied stimulation downward from the second frequency of 77 Hz to a frequency near the selected first frequency of 70 Hz or discontinuing sweep of stimulation at some frequency greater than 70 Hz.

In order to control delivery of the electrical stimulation, processor 40 retrieves one or more therapy programs that define a particular program of therapy in terms of respective values for electrical stimulation parameters, such as a stimulation electrode combination, electrode polarity, current or voltage amplitude, pulse width, and pulse rate. In addition, therapy programs 54 may also include, for example, an adjustable stepping rate (e.g., about 0.1 seconds per step to about 600 seconds per step) associated with the frequency sweep (e.g., the length of time that stimulation generator 44 applies stimulation at a particular frequency before changing the frequency), an adjustable stepping interval (e.g., about 0.1 Hz to about 10 Hz) associated with the frequency sweep (e.g., the spacing between applied frequencies as the sweep is performed), an adjustable duty cycle, and an adjustable duration associated with the electrical stimulation (e.g., 0.1 millisecond, 0.5 seconds, etc.), whether the stimulation is delivered at a constant frequency or via a frequency sweep. It should be noted that in some example, between stimulation sweeps, a continuous constant frequency stimulation may be delivered or all stimulation may be discontinued.

As mentioned above, the delivered electrical stimulation may be in the form of pulses or a continuous waveform. As such, the frequency of the delivered electrical stimulation may refer to the frequency of a pulse or the frequency of a continuous waveform. Stimulation parameters such as voltage or current amplitude, electrode combinations and polarity, and, if applicable, pulse width, may all be adjusted in order to provide efficacious treatment to the patient.

In some examples, processor 40 may control stimulation generator 44 to periodically repeat delivering electrical stimulation at a second frequency that is between a range of about 1.05 times and about 3 times the selected first frequency, or periodically repeat sweeping the second frequency downward toward the first frequency while delivering electrical stimulation. For example, the electrical stimulation may be delivered daily, or every several seconds or minutes. Other periodic intervals, such as once every half-hour, once per hour, and twice daily, may be desirable. Numerous other period intervals are included within the scope of this disclosure although not specifically recited.

Rather than periodically repeating the delivery of the electrical stimulation, processor 40 may continuously deliver the electrical stimulation at a second frequency that is between a range of about 1.05 times and about 3 times the selected first frequency, or sweep the second frequency downward toward the first frequency while delivering electrical stimulation. For example, processor 40 may sweep the second frequency downward toward the first frequency while delivering electrical stimulation. Upon reaching a frequency near the first frequency, processor 40 may immediately begin sweeping the second frequency downward again toward the first frequency while delivering electrical stimulation. Or, in another example, processor 40 may control delivery of electrical stimulation at a second frequency that is between a range of about 1.05 times and about 3 times the selected first frequency for a certain length of time. After that time, processor 40 may control stimulation generator 44 to reapply electrical stimulation, as will be discussed in more detail below.

In one example, electrical stimulation may be applied in response to sensed brain activity. For instance, processor 40 may sense bioelectrical brain signals of patient 12 and only apply electrical stimulation in response to the sensed brain signals, e.g., reduced gamma band activity.

In other examples, aspects of the periodic and continuous delivery of stimulation may be combined. For example, processor 40 may continuously sweep the second frequency downward toward the first frequency while delivering electrical stimulation for some duration of time or until a specific biomarker is identified by processor 40. This continuous sweep may identify a frequency that is effective in producing a desired therapeutic effect. After the duration of time or receipt of a biomarker, processor 40 may then apply electrical stimulation having the previously identified frequency, or a frequency near the identified frequency, rather than applying sweeping stimulation. If at some point the previously identified frequency no longer produces the desired therapeutic effect, processor 40 may then begin continuously sweeping frequencies again.

Regardless of whether the techniques for delivering electrical stimulation described in this disclosure are performed once, periodically, or on a continuous basis on patient 12, the delivery of electrical stimulation using the techniques of this disclosure may re-establish control of the gamma frequency band activity within brain 28 of patient 12. In some examples, processor 40 may analyze bioelectric brain signals in order to determine, for example, one or more biomarkers that may indicate that the endogenous gamma frequency band activity of patient 12, e.g., gamma frequency band rhythm, has been re-induced. Biomarkers may include, for example, an amplitude of a rhythm and/or a phase of a rhythm within one or more frequency bands in brain 28.

Processor 40 may analyze bioelectrical brain signals in order to determine, for example, whether one or more biomarkers is present within one or more of the beta frequency band, the gamma frequency band, and the theta frequency band. For example, sensing module 46 may sense via a subset of electrodes 24, 26 (or a different subset of electrodes) bioelectrical brain signals of brain 28, measure an amplitude of the sensed bioelectrical brain signals, and provide the sensed bioelectrical brain signals and measured amplitude to processor 40. Upon receiving the sensed bioelectrical brain signals and measured amplitude, processor 40 may analyze the received signals to determine whether an amplitude and/or a phase of a rhythm indicative of redevelopment of endogenous gamma frequency band activity is present within one or more of the beta frequency band, the gamma frequency band, and the theta frequency band of brain 28 of patient 12.

For instance, sensing module 46 may include frequency monitoring module 49 capable of monitoring bioelectrical brain signals associated with patient 12 in selected frequency bands. Frequency monitoring module 49 may include tunable filtering and amplification capabilities that filter the bioelectrical brain signals into one or more of the beta frequency band, the gamma frequency band, and the theta frequency band, for example, and amplify the resulting filtered signal for analysis by processor 40. That is, frequency monitoring module 49 may be tuned, either by a clinician, patient, or without user intervention (i.e., automatically), to detect bioelectrical brain signals in one or more frequency bands such as the beta frequency band, the gamma frequency band, and the theta frequency band. Example circuitry capable of filtering and amplifying bioelectrical brain signals is described in U.S. patent application Ser. No. 12/237,868 to Denison et al., entitled, "FREQUENCY SELECTIVE MONITORING OF PHYSIOLOGICAL SIGNALS," which was filed on Sep. 25, 2008.

It should be noted that in some example implementations, the bioelectrical brain signals of patient 12 may be analyzed by processor 60 of programmer 14 (or by a computer) and then transmitted via telemetry module 64 to telemetry module 50 of IMD 16.

As mentioned above, processor 40 may analyze the signals to determine whether an amplitude of a rhythm indicative of redevelopment of endogenous normal gamma frequency band activity is present within one or more frequency bands. In the gamma band, amplitudes may range from about 0.1 uV to about 500 uV. Similar ranges exist for amplitudes in the Beta band and other bands, although the specific values for these amplitudes will vary greatly depending upon physiological state, electrode characteristics and placement, etc. Processor 40 may utilize numerous techniques to perform such an analysis, some of which are described below. In one example, processor 40 may analyze the amplitude of a signal in the gamma frequency band and compare the amplitude to a representative threshold amplitude value retrieved from parameters 59 of memory 42. The representative threshold amplitude value may be, for example, determined based on the basic body model. If the analyzed amplitude is less than the representative threshold amplitude value, processor 40 may control stimulation generator 44 to deliver electrical stimulation at a frequency greater than the selected frequency (which, in some examples, may also be stored in parameters 59). For example, the analyzed amplitude may be 0.1 microvolts ($\mu V$) and the representative threshold amplitude may be 10 $\mu V$. In this case, processor 40 may control stimulation generator 44 to deliver electrical stimulation in a sweeping manner as described throughout this disclosure, or deliver stimulation at a particular frequency greater than the selected gamma frequency without sweeping.

After stimulation generator 44 delivers the electrical stimulation, or in between electrical stimulation pulses, the sensing module 46 and frequency monitoring module 49 may again monitor bioelectrical brain signals associated with patient 12. Then, processor 40 may analyze the signals to determine whether the delivered electrical stimulation resulted in an amplitude of a rhythm indicative of redevelopment of endogenous gamma frequency band activity is present within one or more frequency bands. That is, processor 40 may again compare the amplitude of a bioelectrical brain signal in the gamma frequency band to the representative threshold amplitude value. If the amplitude of the signal is greater than the representative threshold amplitude value, processor 40 may determine that further delivery of electrical stimulation in the sweeping manner described above is unnecessary. For instance, the analyzed amplitude may be 70 microvolts ($\mu V$) and the representative threshold amplitude may be 50 $\mu V$. In this case, because the analyzed amplitude is greater than the threshold amplitude, processor 40 may determine that further delivery of electrical stimulation in the manner described throughout this disclosure is unnecessary. If, however, the amplitude of the signal is less than the representative threshold amplitude value, processor 40 may again deliver electrical stimulation in the manner described above. Subsequent delivery of electrical stimulation may occur immediately, or after some adjustable delay in time, for example about 0.1 minute to 1 hour or longer.

In another example, rather than comparing the amplitude of the bioelectrical brain signals to a representative threshold amplitude value, the amplitude of the signals may be compared to an amplitude value that was found to be efficacious for patient 12. For example, a particular patient 12 may be responsive to a gamma frequency band amplitude value of 60 $\mu V$. A clinician, for example, may store this efficacious value in parameters 59 of memory 42. Upon receiving bioelectrical brain signals associated with patient 12, processor 40 may analyze and compare the received signals to the efficacious value stored in parameters 59. In a manner similar to that described above with respect to the representative threshold value, processor 40 may determine whether or not to deliver electrical stimulation in the sweeping manner described throughout this disclosure. In some examples, the efficacious value may be the patient's normal gamma frequency value. In other examples, the efficacious value may be a value that is not the patient's normal gamma frequency value, but near enough to the patient's normal gamma frequency value so as to produce efficacious results.

Although the examples provided above are directed to analyzing the amplitude of the bioelectrical brain signals in the patient's gamma frequency band, the disclosure is not so limited. Rather, as mentioned above, bioelectrical brain signals from the beta frequency band and the theta frequency band, for example, may be analyzed instead of or in addition to the signals from the gamma frequency band to determine the need for or the effectiveness of delivery of electrical stimulation in the sweeping manner described throughout this disclosure. For example, beta frequency band activity may be analyzed prior to and/or after delivery of sweeping electrical stimulation. Suppression of activity in the beta frequency band may be a biomarker indicative of re-inducement of gamma band activity. That is, attenuation of an amplitude in the beta frequency band may indicate that the delivery of sweeping electrical stimulation has been effective in re-inducing gamma frequency band rhythms (e.g., a rhythm having an amplitude of about 1.0 uV at about 70 Hz), or that the delivery of sweeping electrical stimulation is unnecessary.

For example, sensing module 46 and frequency monitoring module 49 may monitor bioelectrical brain signals associated with the beta frequency band of patient 12. Then, processor 40 may analyze the signals to determine whether the delivered electrical stimulation attenuated a bioelectrical brain signal amplitude of a rhythm in the beta frequency band below either a representative threshold amplitude value or a patient-specific threshold value. For example, sensing module 46 and frequency monitoring module 49 may sense a beta frequency band amplitude (e.g., root mean square, and ½ peak to peak, of 5 $\mu V$. Processor 40 may compare the sensed beta frequency band amplitude of 5 $\mu V$ to a threshold value retrieved from parameters 59 in memory 42. If the sensed amplitude is greater than the threshold value, processor 40 may control stimulation generator 44 to deliver electrical stimulation at a frequency greater than the selected frequency. After stimulation generator 44 delivers the electrical stimulation, sensing module 46 and frequency monitoring module 49 may again monitor bioelectrical brain signals associated with the beta frequency band of patient 12. Then, processor 40 may analyze the signals to determine whether the delivered electrical stimulation resulted in an attenuated amplitude of a rhythm in the beta frequency band, which may be associated with reestablishment of endogenous gamma frequency band activity in the brain of patient 12.

As seen above, an increase in gamma frequency band activity, or a suppression of beta frequency band activity may both be indicative of redevelopment of endogenous gamma frequency band activity. In other examples, processor 40 may analyze the relationship between beta frequency band activity and gamma frequency band activity as a biomarker for redevelopment of endogenous gamma frequency band activity. For example, a ratio of the amplitude of a rhythm in the beta frequency band and the amplitude of a rhythm in the gamma frequency band may be compared to a predetermined value or range of values, and based on the comparison, processor 40 may determine whether or not to deliver electrical stimulation. For example, a ratio of 0.1 or higher, e.g., about 0.2, of an amplitude of a rhythm in the gamma frequency band to amplitude of a rhythm in the beta frequency band may be desirable. Processor 40 may determine the ratio of the amplitude of a rhythm in the beta frequency band and the amplitude of a rhythm in the gamma frequency band and if higher than about 0.1, processor 40 may determine not to deliver electrical stimulation. If the ratio is less than about 0.1, processor 40 may determine to deliver electrical stimulation.

It should be noted that in some examples, redevelopment of endogenous gamma frequency band activity may be indicated when desired behavioral effects are achieved, undesirable negative behavioral side effects are reduced or eliminated, and/or power in the gamma frequency band is maximized.

The examples described above utilize closed-loop techniques for the delivery of sweeping electrical stimulation. That is, the examples describe sensing module 46 and frequency monitoring module 49 monitoring bioelectrical brain signals, processor 40 analyzing the bioelectrical brain signals and controlling delivery of electrical stimulation based on the analysis, sensing module 46 and frequency monitoring module 49 monitoring bioelectrical brain signals after delivery of the electrical stimulation, and processor 40 determining whether stimulation generator 44 should again deliver sweeping electrical stimulation.

In other example configurations, open-loop techniques for the delivery of sweeping electrical stimulation may be employed. For instance, in one open-loop technique, the bioelectrical brain signals of patient 12 may not be monitored for the purpose of identifying a stimulation frequency. Rather, processor 40 may select a frequency within a frequency band of patient 12 and control delivery of electrical stimulation at a frequency greater than the selected frequency without monitoring the bioelectrical brain signals of patient 12. In one example, as described above, processor 40 may control stimulation generator 44 to deliver via electrodes 24, 26 electrical stimulation to patient 12 at a frequency that is between a range of about 1.05 times and about 3 times the selected frequency. In another example, processor 40 may control stimulation generator 44 to begin delivering via electrodes 24, 26 electrical stimulation to patient 12 at a second frequency that is between a range of about 1.05 times and about 3 times the selected first frequency and then sweep the frequency of delivered electrical stimulation downward from the second frequency to a frequency near the selected first frequency. In either case, in an open-loop configuration, the bioelectrical brain signals may not be monitored following delivery of the electrical stimulation. By not monitoring bioelectrical brain signals after delivery of the electrical stimulation, open-loop configurations may be advantageous in that they may reduce the amount of power consumed by IMD 16. Open-loop configurations may be useful in patients that require continuous or nearly continuous delivery of electrical stimulation according to the techniques described in this disclosure. In such patients, eliminating monitoring of bioelectrical brain signals may significantly reduce power consumption and prolong the life of power source 52.

The techniques described in this disclosure may be performed in a system that has already been implanted in a patient and programmed, or in clinical settings in which a system is being implanted in a patient and programming is being turned on for the first time. In a clinical implant setting, for example, in addition to or instead of monitoring biomarkers, a clinician may monitor the motor performance, e.g. clinical Unified Parkinson's Disease Rating Scale (UPDRS), or similar clinical measure, of a patient. As mentioned above, gamma frequency band activity may be facilitative of movement. A clinician may use the techniques of this disclosure to deliver electrical stimulation to patient 12 and monitor the motor performance of patient 12 in response to receiving the electrical stimulation. By monitoring the motor performance of patient 12 in response to receiving the electrical stimulation, a clinician may determine efficacious electrical stimulation settings that may be programmed into memory 42. For example, a clinician may determine the patient's specific gamma frequency within the gamma frequency band, an amplitude of efficacious electrical stimulation, and a duration associated with the delivery of electrical stimulation. The determined stimulation settings may be programmed into memory 42 as part of therapy programs 54 for later use.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
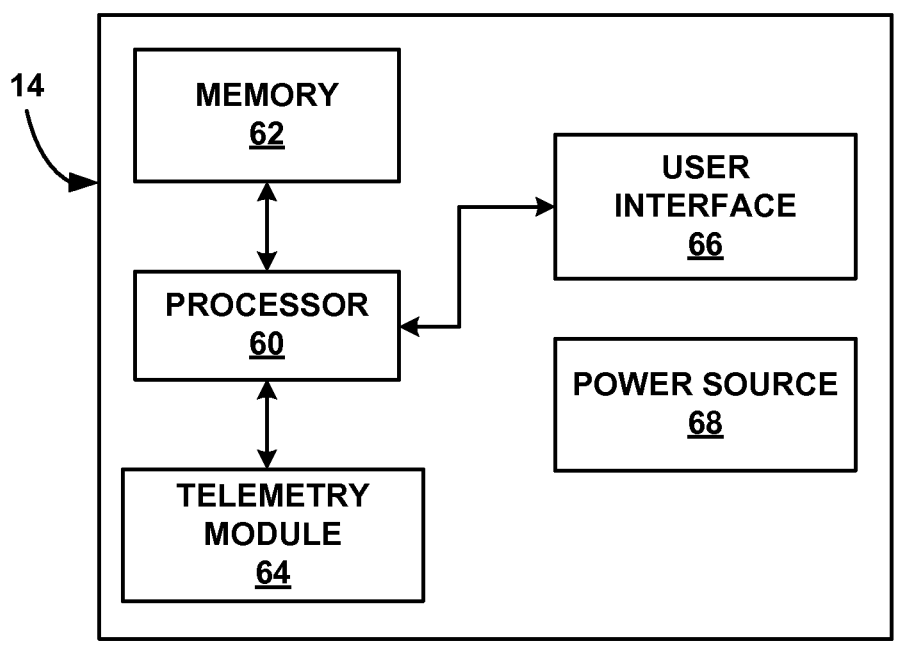
FIG. 3 is a functional block diagram illustrating components of an example medical device programmer that may be used to implement the techniques of this disclosure.

FIG. 3 is a functional block diagram illustrating components of an example medical device programmer that may be used to implement the techniques of this disclosure. Example external medical device programmer 14 of FIG. 3 includes processor 60, memory 62, telemetry module 64, user interface 66, and power source 68. Processor 60 controls user interface 66 and telemetry module 64, and stores and retrieves information and instructions to and from memory 62. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

A user, such as a clinician or patient 12, may interact with programmer 14 through user interface 66. User interface 66 includes a display (not shown), such as a LCD or LED display or other type of screen, to present information related to the therapy, such as information related to bioelectrical signals sensed via a plurality of sense electrode combinations. In addition, user interface 66 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 60 of programmer 14 and provide input.

If programmer 14 includes buttons and a keypad, the buttons may be dedicated to performing a certain function, e.g., a power button, or the buttons and the keypad may be soft keys that change in function depending upon the section of the user interface currently viewed by the user. Alternatively, the display (not shown) of programmer 14 may be a touch screen that allows the user to provide input directly to the user interface shown on the display. The user may use a finger, stylus, or other pointing device to provide input to the display.

In other examples, user interface 66 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 60 of programmer 14. For example, in some examples, processor 60 may receive a bioelectrical brain signal from IMD 16 or from a sensing module that is separate from IMD 16. The separate sensing module may, but need not be, implanted within patient 12. In some examples, processor 60 may analyze one or more biomarkers sensed with the one or more sense electrode combinations associated with at least one of the stimulation electrode combinations. Based on the analysis of the biomarker, processor 60 may determine whether to deliver, or continue delivering, electrical stimulation at a frequency some margin that is greater than the selected gamma band frequency. In some cases, processor 60 may transmit a signal to IMD 16 to instruct IMD 16 to deliver electrical stimulation, or alter delivery of electrical stimulation by selecting a new program or switching stimulation electrode combinations.

Processor 40 of IMD 16 may receive the signal from programmer 14 via its respective telemetry module 50 (FIG. 3). Processor 40 of IMD 16 may deliver electrical stimulation by selecting a stored therapy program from memory 42 based on the signal from processor 60 of programmer 14. Alternatively, processor 60 of programmer 14 may select a therapy program or a specific stimulation electrode combination and transmit a signal to IMD 16, where the signal indicates the therapy parameter values to be implemented by IMD 16 to help improve the efficacy of the stimulation to manage the patient's movement disorder. The indication may be, for example, an alphanumeric identifier or symbol that is associated with the therapy program in memory 42 of IMD 16.

Memory 62 may include instructions for operating user interface 66 and telemetry module 64, and for managing power source 68. Memory 62 may also store any therapy data retrieved from IMD 16 during the course of therapy. The clinician may use this therapy data to determine the progression of the patient condition in order to predict future treatment. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 delivers operating power to the components of programmer 14. Power source 68 may include a battery and a power generation circuit to produce the operating power. In some examples, the battery (e.g., nickel cadmium or lithium ion batteries) may be rechargeable to allow extended operation. Recharging may be accomplished by electrically coupling power source 68 to a cradle or plug that is connected to an alternating current (AC) outlet. In addition, recharging may be accomplished through proximal inductive interaction between an external charger and an inductive charging coil within programmer 14. In other examples, traditional batteries may be used. In addition, programmer 14 may be directly coupled to an alternating current outlet to operate. Power source 68 may include circuitry to monitor power remaining within a battery. In this manner, user interface 66 may provide a current battery level indicator or low battery level indicator when the battery needs to be replaced or recharged. In some cases, power source 68 may be capable of estimating the remaining time of operation using the current battery.

Figure 4:
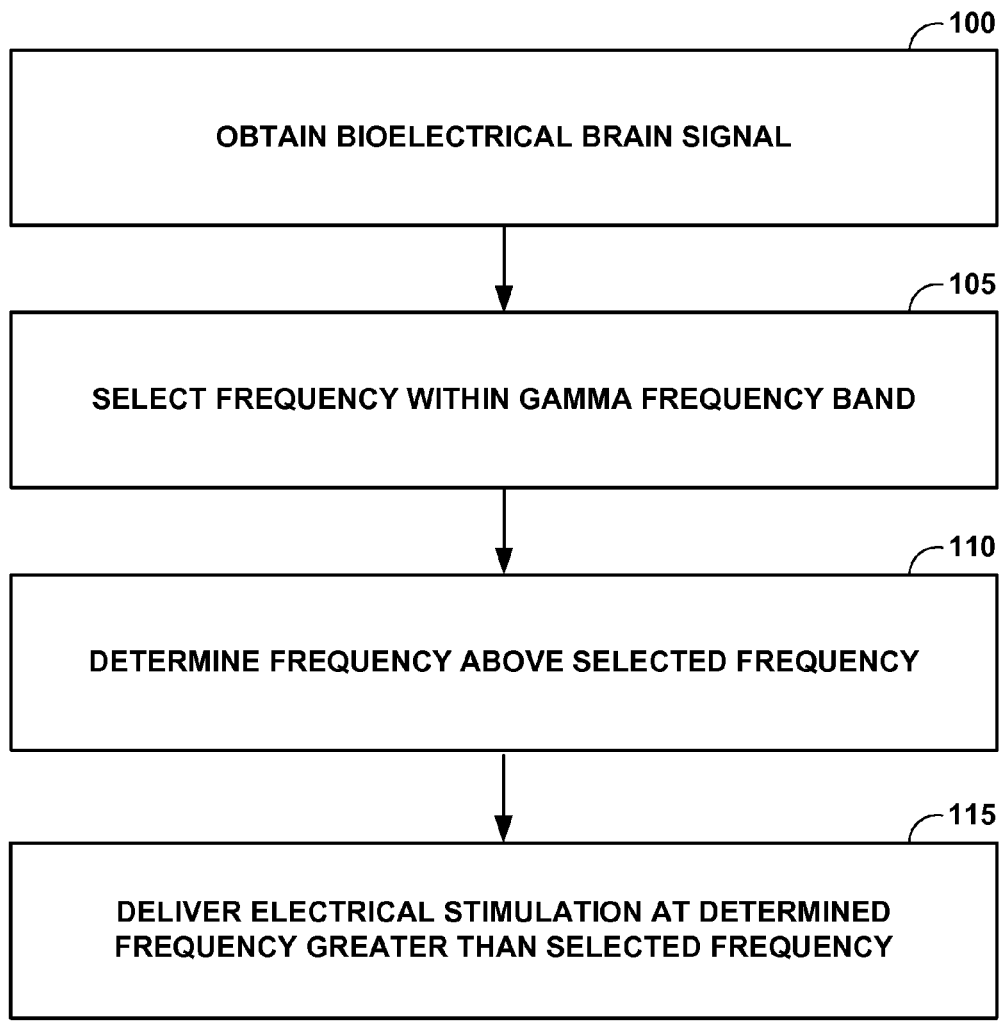
FIG. 4 is a flow diagram of an example technique for reestablishing activity within the gamma frequency band of a patient in accordance with the techniques of this disclosure.

FIG. 4 is a flow diagram of an example technique for reestablishing activity within the gamma frequency band of a patient in accordance with the techniques of this disclosure. Processor 40 of IMD 16, processor 60 of programmer 14, or another computing device may implement the example technique of FIG. 4. Although processor 40 is referred to throughout the description of FIG. 4, in other examples, processor 60 of programmer 14 or another computing device may implement the technique shown in FIG. 4.

Processor 40 may first obtain bioelectrical brain signals from brain 28 of patient 12 (100). Processor 40 may then select a frequency within a gamma frequency band of patient 12 from the bioelectrical brain signals (105). The gamma frequency band has a frequency range between about 35 Hertz and about 120 Hertz. In one example, processor 40 may select a patient-specific frequency within the gamma frequency band by analyzing bioelectrical brain signals sensed across selected electrodes, e.g., electrodes 24, 26. For example, processor 40 may analyze bioelectrical brain signals sensed across the electrodes 24, 26, determine that a specific patient 12 has oscillations of 70 Hz within the gamma frequency band, and then select a frequency of 70 Hz within the gamma frequency band. In another example, processor 40 may select a representative frequency, e.g., a frequency based on the basic body model, within the gamma frequency band rather than a patient-specific frequency.

After selecting the frequency, processor may determine a frequency, or range of frequencies, greater than the selected frequency at which electrical stimulation will be delivered to patient 12 (115). Then, processor 40 may control stimulation generator 44 to deliver electrical stimulation at the determined frequency that is greater than the selected frequency, e.g., greater than 70 Hz (120) in order to reestablish gamma frequency band activity in patient 12. In one example, processor 40 may control stimulation generator 44 to deliver electrical stimulation to patient 12 via electrodes 24, 26 at a frequency that is between a range of about 1.05 times and about 3 times the selected frequency. For example, processor 40 may control stimulation generator 44 to deliver electrical stimulation at a frequency 1.5 times the selected frequency, e.g., 1.5 times the selected frequency of 70 Hz. Reestablishing gamma frequency band activity within patient 12 may facilitate movement and cognitive states.

In another example, processor 40 may control stimulation generator 44 to begin delivering via electrodes 24, 26 electrical stimulation to patient 12 at a second frequency that is between a range of about 1.05 times and about 3 times the selected first frequency, e.g., 1.05 times to 3 times the selected first frequency of 70 Hz, and then sweep the frequency of selected electrical stimulation downward from the second frequency to a frequency near the selected first frequency (or upward toward a third frequency within a range between about 1.05 to about 3 times the selected frequency).

Figure 5:
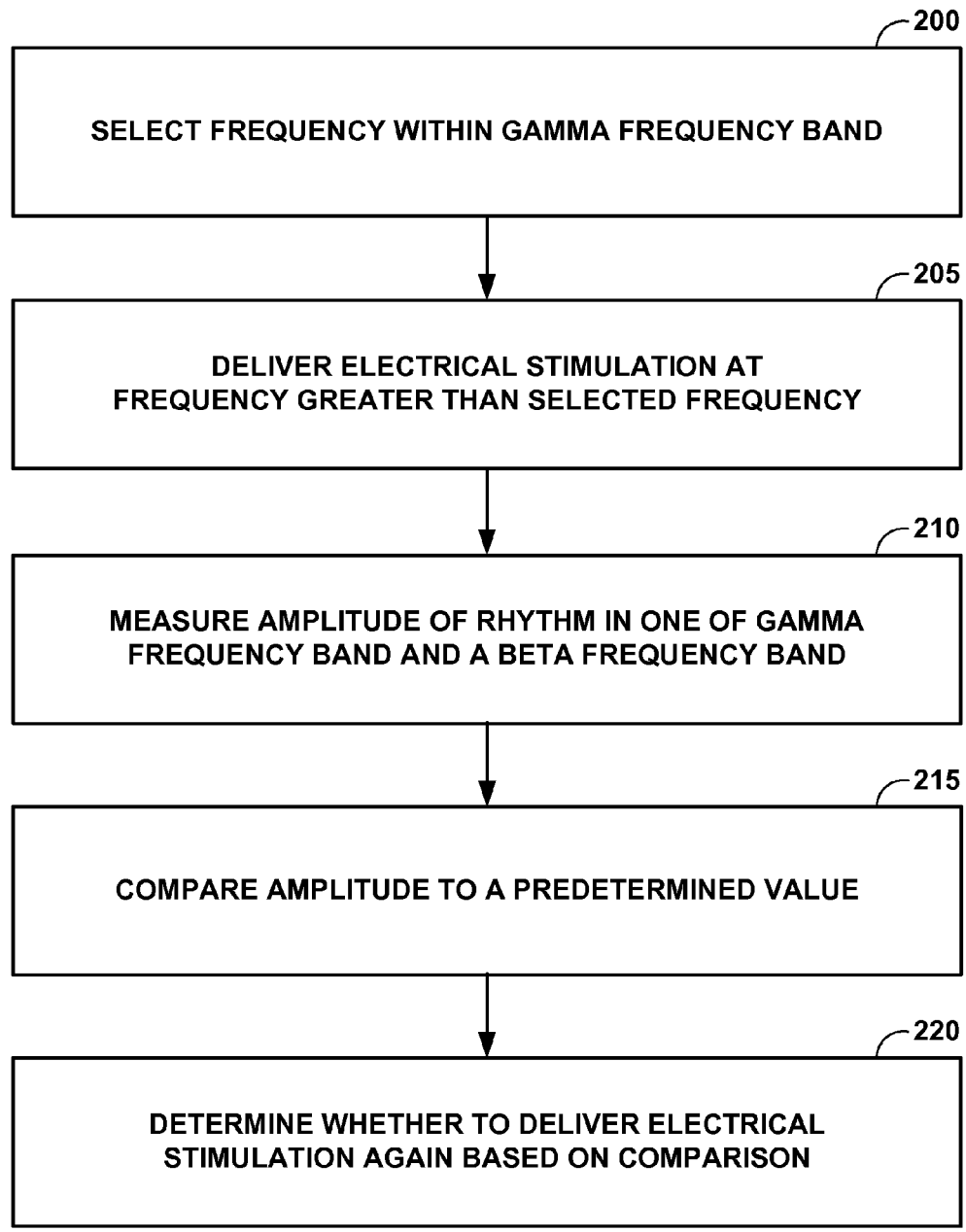
FIG. 5 is a flow diagram of another example technique for reestablishing activity within the gamma frequency band of a patient in accordance with the techniques of this disclosure.

FIG. 5 is a flow diagram of another example technique for reestablishing activity within the gamma frequency band of a patient in accordance with the techniques of this disclosure. Steps 200 and 205 of FIG. 5 are similar to steps 100 and 105 described above with respect to FIG. 4 and for purposes of conciseness, will not be described again.

After processor 40 controls stimulation generator 44 to deliver electrical stimulation at a frequency greater than the selected frequency, sensing module 46 may sense via a subset of electrodes and measure an amplitude of a rhythm in at least one of a gamma frequency band and a beta frequency band (210). The gamma frequency band has a frequency range between about 60 Hertz and about 80 Hertz, and the beta frequency band has a frequency range between about 10 Hertz and about 30 Hertz. Sensing module 46 may provide the sensed bioelectrical brain signals and measured amplitude to processor 40. Upon receiving the sensed bioelectrical brain signals and measured amplitude, processor 40 may analyze the received signals to determine whether the amplitude is indicative of redevelopment of endogenous gamma frequency band activity in patient 12. For example, processor 40 may compare the measured amplitude to a predetermined value (215). In one example, processor 40 may compare the amplitude to a representative threshold amplitude value, e.g., a value determined from the basic body model, retrieved from parameters 59 of memory 42. In another example, rather than comparing the amplitude of the bioelectrical brain signals to a representative threshold amplitude value, the amplitude of the signals may be compared to an amplitude value that was found to be efficacious for patient 12. A clinician, for example, may store this efficacious value in parameters 59 of memory 42.

After comparing the amplitude to a predetermined value, processor 40 determines whether to deliver the electrical stimulation again based on the comparison (220). For example, if the measured amplitude of a rhythm in the gamma frequency band is greater than the predetermined value retrieved from memory 42, processor 40 may determine that further delivery of electrical stimulation in the manner described throughout this disclosure is unnecessary. If, however, the amplitude of the signal is less than the predetermined amplitude value, processor 40 may again deliver electrical stimulation in the manner described above.

Figure 6:
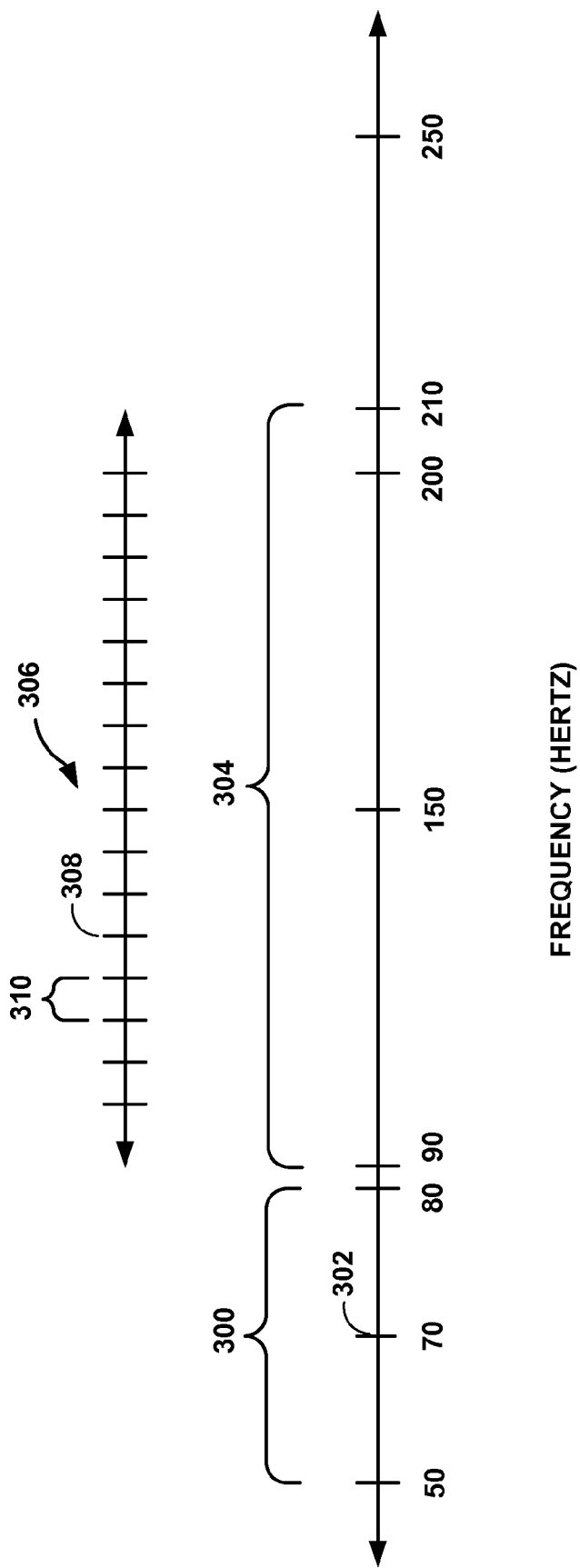
FIG. 6 is a graph comparing a selected frequency in the gamma band and frequencies greater than the selected gamma band frequency for delivery of stimulation.

FIG. 6 is a graph comparing a selected frequency in the gamma band and frequencies greater than the selected gamma band frequency for delivery of stimulation. In FIG. 6, the gamma band, having frequencies from about 50 Hz to about 80 Hz is shown at 300. An example selected frequency (e.g., the patient's specific gamma frequency or representative gamma frequency) in the gamma band of 70 Hz is depicted at 302. As described in detail above, electrical stimulation may be delivered at a frequency that is some margin that is greater than the selected frequency, e.g., 1.05 times to 3 times the selected frequency. The range of frequencies between 1.05 times to 3 times the selected frequency (about 90 Hz to about 210 Hz) is graphically illustrated at 304. Finally, as described above, the electrical stimulation may be delivered in a sweeping manner across a range of frequency values. As shown generally at 306, the electrical stimulation may begin at a frequency 308 that is between about 1.05 times and 3 times selected gamma band frequency 302 and extend upward to another, higher frequency that is between 1.05 times and 3 times selected gamma band frequency 302, or downward to another, lower frequency that is between 1.05 times and 3 times selected gamma band frequency 302. The frequencies in the range of frequency values may be separated by an interval, as shown at 310. Although FIG. 6 depicts approximately constant intervals 310, in some examples intervals 310 may vary in value.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples of the disclosure have been described. These and other examples are within the scope of the following claims.

The invention claimed is:

1. A method comprising:
   selecting a frequency within a gamma frequency band, wherein the selected frequency is one of a patient-specific frequency or a representative frequency;
   delivering electrical stimulation, via one or more electrodes, at a frequency greater than the selected frequency;
   in response to delivering the electrical stimulation, measuring an amplitude of a rhythm in at least one of the gamma frequency band and a beta frequency band;
   determining, by one or more processors whether the measured amplitude is indicative of a desired gamma frequency band activity having been re-induced, and based on whether the measured amplitude is indicative of the desired gamma frequency band activity having been re-induced, determining whether to deliver additional electrical stimulation, via the one or more electrodes, at the frequency greater than the selected frequency, and
   in response to a determination to deliver additional electrical stimulation at the frequency greater than the selected frequency, delivering, via the one or more electrodes, the additional electrical stimulation.

2. The method of claim 1, wherein the gamma frequency band comprises frequencies within a range of about 35 Hertz to about 120 Hertz.

3. The method of claim 1, wherein delivering electrical stimulation at a frequency greater than the selected frequency comprises:
   delivering electrical stimulation at a constant pulse frequency within a range between about 1.05 times to about 3 times the selected frequency.

4. The method of claim 1, wherein the selected frequency within the gamma frequency band is a first frequency, and wherein delivering electrical stimulation at a frequency greater than the selected frequency to a patient comprises:
   delivering electrical stimulation at a second frequency within a range between about 1.05 to about 3 times the selected frequency; and
   at least one of sweeping the second frequency downward toward the first frequency while delivering electrical stimulation and sweeping the second frequency upward toward a third frequency within a range between about 1.05 to about 3 times the selected frequency.

5. The method of claim 4, wherein sweeping the second frequency downward or upward while delivering electrical stimulation is periodically repeated.

6. The method of claim 4, wherein sweeping the second frequency downward or upward while delivering electrical stimulation is continuously repeated.

7. The method of claim 4, wherein sweeping the second frequency downward or upward while delivering electrical stimulation comprises:
   delivering electrical stimulation at different frequencies in one of a linear manner or non-linear manner.

8. The method of claim 1, wherein the measured amplitude comprises a first biomarker of a patient, and wherein the method further comprises, in response to delivering electrical stimulation, monitoring at least one of a motor performance of the patient and a second biomarker of the patient.

9. The method of claim 1, wherein the beta frequency band has a frequency range between about 8 Hertz and about 35 Hertz, and wherein the method further comprises:
   comparing the measured amplitude to a predetermined value; and
   determining whether to deliver the additional electrical stimulation based on the comparison.

10. The method of claim 1, wherein delivering electrical stimulation to a patient at a frequency greater than the selected frequency comprises:
   continuously delivering electrical stimulation to the patient at a frequency greater than the selected frequency.

11. The method of claim 1, further comprising, responsive to the determination, delivering the additional electrical stimulation at the frequency greater than the selected frequency.

12. The method of claim 1, wherein selecting a frequency within a gamma frequency band comprises selecting the patient-specific frequency,
   analyzing bioelectrical brain signals sensed via the one or more electrodes;
   detecting oscillations at a particular frequency; and
   selecting the particular frequency as the selected patient-specific frequency.

13. The method of claim 1, wherein selecting a frequency within a gamma frequency band comprises selecting the representative frequency, the representative frequency selected based on at least one of age, sex, disease severity, type of symptoms, medication state, behavioral sate, psychological state or physical state.

14. The method of claim 1, wherein a patient-specific frequency is selected based on a bioelectrical brain signal of a patient, or a representative frequency is selected based on a model.

15. A device comprising:
   an implantable housing;
   one or more leads coupled to the housing;
   one or more electrodes carried by the one or more leads; and
   a processor configured to:
      select a frequency within a gamma frequency band, wherein the selected frequency is one of a patient-specific frequency or a representative frequency;
      control delivery of electrical stimulation at a frequency greater than the selected frequency;
      in response to the delivery of the electrical stimulation, measure an amplitude of a rhythm in at least one of the gamma frequency band and a beta frequency band; and
      determine whether the measured amplitude is indicative of a desired gamma frequency band activity having been re-induced, and based on whether the measured amplitude is indicative of the desired gamma frequency band activity having been re-induced, determine whether to deliver additional electrical stimulation at the frequency greater than the selected frequency.

16. The device of claim 15, wherein the gamma frequency band comprises frequencies within a range of about 35 Hertz to about 120 Hertz.

17. The device of claim 15, wherein the processor configured to control delivery of electrical stimulation at a frequency greater than the selected frequency is further configured to:
   deliver electrical stimulation at a constant pulse frequency within a range between about 1.05 times to about 3 times the selected frequency.

18. The device of claim 15, wherein the selected frequency within the gamma frequency band is a first frequency, and wherein the processor configured to control delivery of electrical stimulation at a frequency greater than the selected frequency to a patient is further configured to:
   control delivery of electrical stimulation at a second frequency within a range between about 1.05 to about 3 times the selected frequency; and
   at least one of sweep the second frequency downward toward the first frequency while delivering electrical stimulation and sweep the second frequency upward toward a third frequency within a range between about 1.05 to about 3 times the selected frequency.

19. The device of claim 18, wherein the processor configured to sweep the second frequency downward or upward while delivering electrical stimulation is configured to periodically repeat the sweep.

20. The device of claim 18, wherein the processor configured to sweep the second frequency downward or upward while delivering electrical stimulation is configured to continuously repeat the sweep.

21. The device of claim 18, wherein the processor configured to sweep the second frequency downward or upward while delivering electrical stimulation is configured to:
   control delivery of electrical stimulation at different frequencies in one of a linear manner or non-linear manner.

22. The device of claim 15, wherein the measured amplitude comprises a first biomarker of a patient, and wherein the processor is further configured to
   monitor, in response to delivering electrical stimulation, at least one of a motor performance of the patient and a second biomarker of the patient.

23. The device of claim 15, wherein the beta frequency band has a frequency range between about 8 Hertz and about 35 Hertz, and wherein the processor is configured to:
   compare the measured amplitude to a predetermined value; and
   determine whether to deliver the additional electrical stimulation based on the comparison.

24. The device of claim 15, wherein the processor configured to control delivery of electrical stimulation to a patient at a frequency greater than the selected frequency is further configured to:
control continuous delivery of electrical stimulation to a patient at a frequency greater than the selected frequency.

25. The device of claim 15, wherein the processor is configured to, responsive to the determination, control delivery of the additional electrical stimulation at the frequency greater than the selected frequency.

26. A non-transitory computer-readable storage medium comprising instructions that, when executed by a processor, cause the processor to:
select a frequency within a gamma frequency band, wherein the selected frequency is one of a patient-specific frequency or a representative frequency;
control delivery of electrical stimulation at a frequency greater than the selected frequency;
in response to delivery of the electrical stimulation, measure an amplitude of a rhythm in at least one of the gamma frequency band and a beta frequency band; and
determine whether the measured amplitude is indicative of a desired gamma frequency band activity having been re-induced, and based on whether the measured amplitude is indicative of the desired gamma frequency band having been re-induced, determine whether to deliver additional electrical stimulation at the frequency greater than the selected frequency.

27. The computer-readable storage medium of claim 26, wherein the gamma frequency band comprises frequencies within a range of about 35 Hertz to about 120 Hertz.

28. The computer-readable storage medium of claim 26, wherein the instructions that cause the processor to control delivery of electrical stimulation at a frequency greater than the selected frequency comprise instructions that, when executed by the processor, cause the processor to:
deliver electrical stimulation at a constant pulse frequency within a range between about 1.05 times to about 3 times the selected frequency.

29. The computer-readable storage medium of claim 26, wherein the selected frequency within the gamma frequency band is a first frequency, and wherein the instructions that cause the processor to control delivery of electrical stimulation at a frequency greater than the selected frequency to a patient comprise instructions that, when executed by the processor, cause the processor to:
control delivery of electrical stimulation at a second frequency within a range between about 1.05 to about 3 times the selected frequency; and
at least one of sweep the second frequency downward toward the first frequency while delivering electrical stimulation and sweep the second frequency upward toward a third frequency within a range between about 1.05 to about 3 times the selected frequency.

30. The computer-readable storage medium of claim 29, wherein the instructions that cause the processor to sweep the second frequency downward or upward while delivering electrical stimulation comprise instructions that, when executed by the processor, cause the processor to periodically repeat the sweep.

31. The computer-readable storage medium of claim 29, wherein the instructions that cause the processor to sweep the second frequency downward or upward while delivering electrical stimulation comprise instructions that, when executed by the processor, cause the processor to continuously repeat the sweep.

32. The computer-readable storage medium of claim 29, wherein the instructions that cause the processor to sweep the second frequency downward or upward while delivering electrical stimulation comprise instructions that, when executed by the processor, cause the processor to:
control delivery of electrical stimulation at different frequencies in one of a linear manner or non-linear manner.

33. The computer-readable storage medium of claim 26, wherein the measured amplitude comprises a first biomarker of a patient, and wherein the computer-readable storage medium further comprises instructions that, when executed by the processor, cause the processor to:
monitor, in response to delivery of electrical stimulation, at least one of a motor performance of the patient and a second biomarker of the patient.

34. The computer-readable storage medium of claim 26, wherein the beta frequency band has a frequency range between about 8 Hertz and about 35 Hertz, and wherein the computer-readable storage medium further comprises instructions that, when executed by the processor, cause the processor to:
compare the measured amplitude to a predetermined value; and
determine whether to deliver the additional electrical stimulation based on the comparison.

35. The computer-readable storage medium of claim 26, wherein the instructions that cause the processor to control delivery of electrical stimulation to a patient at a frequency greater than the selected frequency further comprise instructions that, when executed by the processor, cause the processor to:
control continuous delivery of electrical stimulation to a patient at a frequency greater than the selected frequency.

36. The computer-readable storage medium of claim 26, further comprising instructions that, when executed by the processor, cause the processor to, responsive to the determination, control delivery of the additional electrical stimulation at the frequency greater than the selected frequency.

37. A device comprising:
means for selecting a frequency within a gamma frequency band;
means for delivering electrical stimulation at a frequency greater than the selected frequency;
means for, in response to delivering the electrical stimulation, measuring an amplitude of a rhythm in at least one of the gamma frequency band and a beta frequency band; and
means for determining whether the measured amplitude is indicative of a desired gamma frequency band activity having been re-induced, and based on whether the measured amplitude is indicative of the desired gamma frequency band activity having been re-induced, determining whether to deliver additional electrical stimulation at the frequency greater than the selected frequency.

38. The device of claim 37, wherein the gamma frequency band comprises frequencies within a range of about 35 Hertz to about 120 Hertz.

39. The device of claim 37, wherein the means for delivering electrical stimulation at a frequency greater than the selected frequency comprises:
means for delivering electrical stimulation at a constant pulse frequency within a range between about 1.05 times to about 3 times the selected frequency.

40. The device of claim 37, wherein the selected frequency within the gamma frequency band is a first frequency, and wherein the means for delivering electrical stimulation at the frequency greater than the selected frequency to a patient comprises:

means for delivering electrical stimulation at a second frequency within a range between about 1.05 to about 3 times the selected frequency; and at least one of means for sweeping the second frequency downward toward the first frequency while delivering electrical stimulation and means for sweeping the second frequency upward toward a third frequency within a range between about 1.05 to about 3 times the selected frequency.

41. The device of claim 40, wherein the means for sweeping the second frequency downward or upward while delivering electrical stimulation comprises means for periodically repeating sweeping the second frequency downward or upward while delivering electrical stimulation.

42. The device of claim 40, wherein the means for sweeping the second frequency downward or upward while delivering electrical stimulation comprises means for continuously repeating sweeping the second frequency downward or upward while delivering electrical stimulation.

43. The device of claim 40, wherein the means for sweeping the second frequency downward or upward while delivering electrical stimulation comprises:

means for delivering electrical stimulation at different frequencies in one of a linear manner or non-linear manner.

44. The device of claim 37, wherein the measured amplitude comprises a first biomarker of a patient, and wherein the device further comprises:

means for, in response to delivering electrical stimulation, monitoring at least one of a motor performance of the patient and a second biomarker of the patient.

45. The device of claim 37, wherein the beta frequency band has a frequency range between about 8 Hertz and about 35 Hertz, and wherein the device further comprises:

means for comparing the measured amplitude to a predetermined value; and means for determining whether to deliver the additional electrical stimulation based on the comparison.

46. The device of claim 37, wherein the means for delivering electrical stimulation to a patient at a frequency greater than the selected frequency comprises:

means for continuously delivering electrical stimulation to a patient at a frequency greater than the selected frequency.

47. The device of claim 37, further comprising means for, responsive to the determination, delivering the additional electrical stimulation at the frequency greater than the selected frequency.

* * * * *